(12) United States Patent
Suda et al.

(10) Patent No.: US 8,691,061 B2
(45) Date of Patent: *Apr. 8, 2014

(54) ELECTRODE DEVICE FOR AN ELECTROCHEMICAL SENSOR CHIP

(75) Inventors: Atsushi Suda, Tokyo (JP); Tatsuo Kimura, Tokyo (JP); Ryota Kunikata, Tokyo (JP); Tomokazu Matsue, Sendai (JP)

(73) Assignees: Japan Aviation Electronics Industry, Limited (JP); National University Corporation Tohoku University (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,237

(22) Filed: Dec. 5, 2011

(65) Prior Publication Data

US 2012/0160676 A1    Jun. 28, 2012

(30) Foreign Application Priority Data

Dec. 28, 2010 (JP) .................. 2010-292497

(51) Int. Cl.
*G01N 27/416* (2006.01)
*G01N 27/30* (2006.01)
*G01N 33/487* (2006.01)

(52) U.S. Cl.
CPC ............ *G01N 27/307* (2013.01); *G01N 33/487* (2013.01)
USPC .............................. 204/287; 204/267; 439/87

(58) Field of Classification Search
USPC ......... 204/434, 267, 286.1, 287, 290.01, 294; 439/44–48, 78, 85, 87
See application file for complete search history.

(56) References Cited

U.S. PATENT DOCUMENTS 5,738,530 A * 4/1998 Schreiber et al. ............. 439/66

8,470,144 B2 * 6/2013 Suda et al. ................. 204/287

FOREIGN PATENT DOCUMENTS

| JP | 2573443 B | | 8/1993 |
| JP | 2003-532090 A | | 10/2003 |
| JP | 2005-034129 A | | 2/2005 |
| JP | 2006-322813 | * | 11/2006 |
| JP | 2006-322813 A | | 11/2006 |
| JP | 2007-278981 A | | 10/2007 |
| WO | 0183674 A1 | | 11/2001 |

OTHER PUBLICATIONS

Outline of Tohoku University Micro System Integration Center Symposium held Dec. 6-8, 2010 in Sendai, Japan, (5 pages) and English translation (8 pages).
Tohoku University Micro System Integration Center Symposium, Activities in collaboration connection sheet for an electrochemical sensor chip (Connection sheet for a biochip), Japan Aviation Electronics Industry, Limited, Product Development Center, Dec. 6, 2010 (15 pages).
Office Action of Feb. 7, 2012 (3 pages) in co-pending Japanese Application No. 2010-292,497 filed Dec. 28, 2010, and partial English translation thereof (1 page) (4 pages total).

\* cited by examiner

*Primary Examiner* — J. Christopher Ball
(74) *Attorney, Agent, or Firm* — Hovey Williams LLP

(57) ABSTRACT

An electrode device for an electrochemical sensor chip includes an insulation sheet having an insulating property and including a top surface and a bottom surface opposite to each other in a thickness direction, and electrode members having a conductivity and held by the insulation sheet with the electrode members piercing the insulation sheet in a thickness direction, one ends of the electrode members located on the top surface side of the insulation sheet being connected to an analyte, the other ends located on the bottom surface side of the insulation sheet being connected to an electrodes of a transducer.

19 Claims, 5 Drawing Sheets

_US 8,691,061 B2_

ELECTRODE DEVICE FOR AN ELECTROCHEMICAL SENSOR CHIP

BACKGROUND OF THE INVENTION

The present invention relates to an electrode device for an electrochemical sensor chip and particularly to a disposable electrode device for connecting any of analytes such as chemicals and biologically derived substances exemplified by DNA, proteins, antibodies, cells, and microorganisms to the electrodes of a transducer for detecting an analyte with an enhanced sensitivity using an electrochemical method.

There are widely known in the fields of medicine, food, and environment techniques for detecting a trace amount of analyte existing in a sample with a high sensitivity. Generally, an electrochemical sensor chip comprises electrodes modified by a molecular recognition element formed of biologically derived substances, chemicals, and the like selectively reacting with an analyte in a sample. When a sample is brought into contact with these electrodes, effects produced by an interaction can be sensed by detecting a change in electric current using an electrochemical method with a high sensitivity if the sample contains a substance interacting with the molecular recognition element.

In the field of gene analyses that have made a rapid progress in recent years, trials are being made to determine DNA sequences by electrochemical methods using, for example, a technique described in JP 2573443 B. These methods enable high-sensitive analysis as to whether DNA, examined as an analyte, has a sequence that is capable of complementarily binding with probe DNA by converting one single stranded DNA obtained by denaturing the analyte DNA and another single stranded DNA having a known base sequence (probe DNA) into double-stranded DNA through hybridization, and then mixing therein an intercalated material specifically binding with double-stranded DNA and reversible with respect to redox reaction.

Electrochemical sensor chips widely use a flat electrode-type electrode device as described, for example, in JP 2007-278981 A to achieve contact with a sample. As illustrated in FIG. 15, this electrode device comprises a planar electrode 2 made of a conductive material formed on an insulation substrate 1. A sample is placed on the planar electrode 2, and the potential of the planar electrode 2 is extracted through a conductive pattern 3. The planar electrode 2 and the conductive pattern 3 can be formed by a printing method, for example, which reduces manufacturing costs so that the electrode device may be suitably used as a disposable electrode device for an electrochemical sensor chip.

JP 2003-532090 A describes another known example of electrochemical measurement, which uses an electrode formed on the surface of an integrated circuit chip. As illustrated in FIG. 16, an electrode 5 is formed on the surface of an integrated circuit chip 4, and a sample 6 is placed on the electrode 5. In this case, an additional circuit for amplifying feeble current may be integrated into the integrated circuit chip 4, so that a highly-sensitive measurement can be expected.

SUMMARY OF THE INVENTION

However in the electrode device as described in JP 2007-278981 A, the potential of the planar electrode device 2 in contact with a sample is extracted through the conductive pattern 3. Therefore, the electrode device necessarily has a long conduction path and is susceptible to electromagnetic noise and the like, possibly reducing the detection sensitivity.

In addition, since the planar electrode device 2 and the conductive pattern 3 are formed in a planar extension on the insulation substrate 1, the size of the electrode device is increased and, when performing multi-point measuring, the whole measuring device requires a large size.

On the other hand, when the sample 6 is a liquid sample containing a biologically derived substance, etc., the integrated circuit chip 4 as described in JP 2003-532090 A may allow the sample 6 to infiltrate into the integrated circuit chip 4 through fine cracks or the like in the insulation layer film covering the surface of the integrated circuit chip 4, possibly causing short-circuiting and thus reducing the reliability of measurement. Further, the electrode 5 is secured to the surface of the integrated circuit chip 4 which is expensive, making it difficult for the electrode device to be used as a disposable product. Further, it is impossible to dispose the electrode device by removing only the electrode 5 from the integrated circuit chip 4.

Thus, an object of the present invention is to provide an electrode device for an electrochemical sensor chip capable of highly-sensitive and highly-reliable measurement even when measuring a liquid sample and suitable for multi-point measurement and the use as a disposable product.

An electrode device for an electrochemical sensor chip according to the present invention comprises: an insulation sheet having an insulating property and including a top surface and a bottom surface opposite to each other in a thickness direction; and electrode members having a conductivity and held by the insulation sheet with the electrode members piercing the insulation sheet in a thickness direction, one ends of the electrode members located on the top surface side of the insulation sheet being connected to an analyte, the other ends located on the bottom surface side of the insulation sheet being connected to an electrodes of a transducer.

DETAILED DESCRIPTION OF THE INVENTION

Embodiments of the present invention will be described below based on the appended drawings.

Embodiment 1

Figure 1:
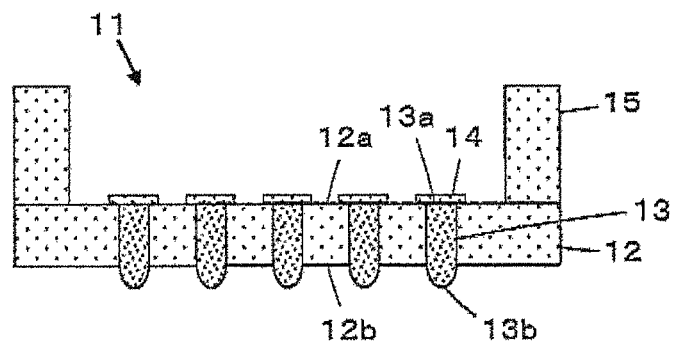
FIG. 1 is a cross section of an electrode device for an electrochemical sensor chip according to an embodiment 1 of the invention.

FIG. 1 illustrates a configuration of an electrode device 11 for an electrochemical sensor chip according to an embodiment 1 of the invention. The electrode device 11 for an electrochemical sensor chip comprises an insulation sheet 12 and electrode members 13 disposed in a matrix distribution at a given pitch in the insulation sheet 12. The insulation sheet 12 is made of an insulating material and comprises a top surface 12a and a bottom surface 12b opposite to each other in a thickness direction. The electrode members 13 are made of a conductive material and are held by the insulation sheet 12 in such a manner that the electrode members 13 pierce the insulation sheet 12 in the thickness direction from the top surface 12a through the bottom surface 12b. One ends 13a of the electrode members 13 are in the same plane as the top surface 12a of the insulation sheet 12 while the other ends 13b of the electrode members 13 project from the bottom surface 12b of the insulation sheet 12.

A biocompatible coating 14 made of a conductive material is provided on the one ends 13a of the electrode members 13 located on the top surface side of the insulation sheet 12 so as to cover the one ends 13a.

Figure 2:
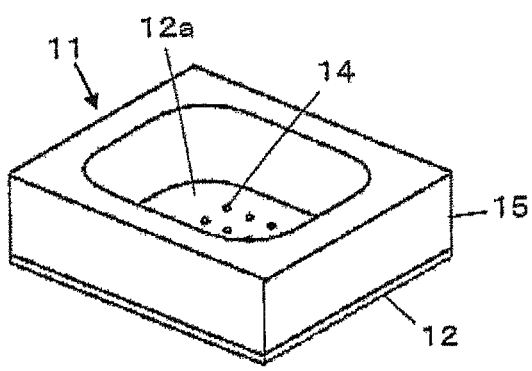
FIG. 2 is a perspective view of the electrode device for an electrochemical sensor chip according to the embodiment 1 of the invention.

An annular liquid reservoir member 15 is provided on the periphery of the top surface 12a of the insulation sheet 12. The liquid reservoir member 15 surrounds all the electrode members 13 covered by the biocompatible coatings 14 on the top surface side of the insulation sheet 12 as illustrated in FIG. 2.

Figure 3:
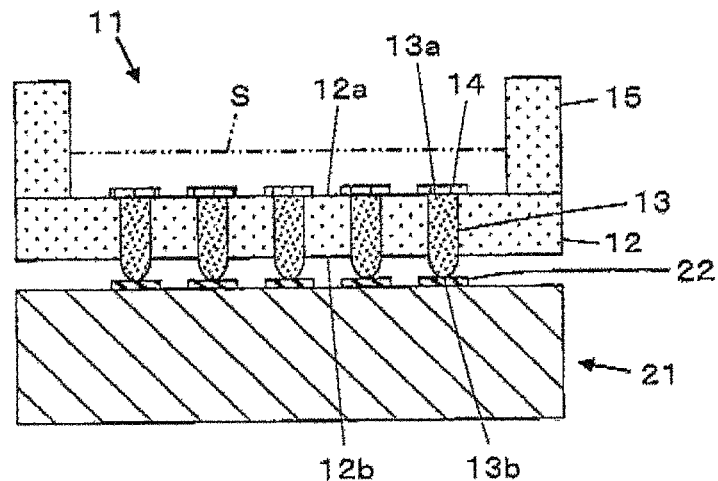
FIG. 3 is a cross section of an electrochemical sensor chip using the electrode device for an electrochemical sensor chip according to the embodiment 1.

The electrode device 11 for an electrochemical sensor chip having the above configuration is disposed immediately on a transducer 21 for use as illustrated in FIG. 3.

The transducer 21 is formed of an LSI chip and comprises electrodes 22 disposed in a matrix distribution on the top surface thereof. The electrodes 22 are disposed at a given pitch that is the same as the given pitch of the electrode members 13 provided on the electrode device 11 for an electrochemical sensor chip, so that the electrode members 13 provided on the electrode device 11 are in one-to-one correspondence with the electrodes 22 of the transducer 21.

The other ends 13b of the electrode members 13 of the electrode device 11 for an electrochemical sensor chip come into contact with the respective electrodes 22 of the transducer 21 to establish electrical connection. Then, a liquid sample S containing an analyte is reserved in the liquid reservoir member 15 of the electrode device 11 for an electrochemical sensor chip. The surface of the biocompatible coatings 14 covering the one ends 13a of the electrode members 13 holds beads previously modified by a molecular recognition element formed of biologically derived substances or the like that selectively react with an analyte existing in the liquid sample S, or the biocompatible coatings 14 are previously modified by a molecular recognition element, so that a change in electric current or the like electrochemically caused as the analyte in the liquid sample S reacts with the molecular recognition element is transmitted to the electrodes 22 of the transducer 21 through the biocompatible coatings 14 and the electrode members 13, whereupon the transducer 21 detects the analyte in the liquid sample S with a high sensitivity.

The material of the insulation sheet 12 of the electrode device 11 for an electrochemical sensor chip may be a silicone rubber. Other examples thereof include resin materials such as acrylic and polycarbonate, glass, and ceramics.

The electrode members 13 may be formed of a silicone based material containing conductive filler such as Ag. Alternatively, the electrode members 13 may be formed of a metallic material having an excellent conductivity such as a metallic material having an Au coated surface.

However, at least one of the insulation sheet 12 and the electrode members 13 preferably have elasticity in order to establish a good electric connection between the electrode members 13 held by the insulation sheet 12 and the electrodes 22 of the transducer 21. Such a configuration absorbs variation in height of the other ends 13b of the electrode members 13 and variation in height of the surfaces of the electrodes 22 of the transducer 21 arising in manufacture and establishes a good electric connection between them, enabling measuring with higher accuracy and enhanced reliability.

When the electrode member 13 has elasticity, the whole of the electrode member 13 need not necessarily have elasticity and it suffices when at least the other ends 13b of the electrode members 13 in contact with the electrodes 22 of the transducer 21 have elasticity.

When the insulation sheet 12 has elasticity, if the bottom surface 12b of the insulation sheet 12 has an adhesion, applying a load from above onto the electrode device 11 for an electrochemical sensor chip placed on the transducer 21 allows the bottom surface 12b of the insulation sheet 12 to adhere to the surface of the transducer 21 and be secured, thus establishing the electrical connection between the electrode members 13 and the electrodes 22 of the transducer 21 with yet further enhanced reliability.

Preferably, the electrode members 13 are held in intimate contact with the insulation sheet 12 in order to prevent the liquid sample S contained in the liquid reservoir member 15 from leaking to the bottom surface side of the insulation sheet 12 through the interfaces between the insulation sheet 12 and the electrode members 13. Accordingly, using the same material ingredients to form the insulation sheet 12 and the electrode members 13 is effective. For example, the insulation sheet 12 made of silicone rubber may hold the electrode members 13 made of a material whose main ingredient is a silicone-based substance.

The intimate contact required between the electrode members 13 and the insulation sheet 12 is sufficient if the liquid sample S does not leak or penetrate through the interfaces between them and gas may flow therethrough. Even in the presence of small gaps between the electrode members 13 and the insulation sheet 12, such intimate contact between them sufficient to preclude the liquid sample S from leaking or penetrating can be achieved by forming coating films on these interfaces that have a low affinity with the liquid sample S or by forming an asperity on the interfaces to reduce the wettability in relation to the liquid sample S.

The biocompatible coatings 14 covering the one ends 13a of the electrode members 13 are provided to achieve chemically stable contact with the analyte in the liquid sample S and may be formed, for example, by applying a carbon paste. While the biocompatible coatings 14 may be otherwise formed by using chemically stable metals such as Au and Pt, a carbon paste, which is inexpensive, is a preferred material when the electrode device 11 for an electrochemical sensor chip is used as a disposable device.

As described above, the electrode device 11 for an electrochemical sensor chip according to the embodiment 1 is disposed immediately on the transducer 21, and the electrode members 13 penetrating the insulation sheet 12 in its thickness direction are brought into contact with the electrodes 22 of the transducer 21 to achieve reduction of conduction path, which reduces the effects produced by, for example, electromagnetic noise, which in turn reduces adverse effects on measuring sensitivity, and hence achieves enhancement of measuring sensitivity. In addition, the configuration of the electrode members 13 being disposed in a matrix distribution so as to correspond to the positions of the electrodes 22 of the transducer 21 enables production of a measuring device having a compact planar size and capable of simultaneous multipoint measuring at the same time. Further, because the insulation sheet 12 and the electrode members 13 are in intimate contact, and the liquid sample S such as electrolyte solution used as specimen is not in immediate contact with the transducer 21, short-circuiting in the circuits inside the transducer 21 cannot occur and thus reliability is enhanced.

The electrode device 11 for an electrochemical sensor chip described above may be produced as follows.

Figure 4:
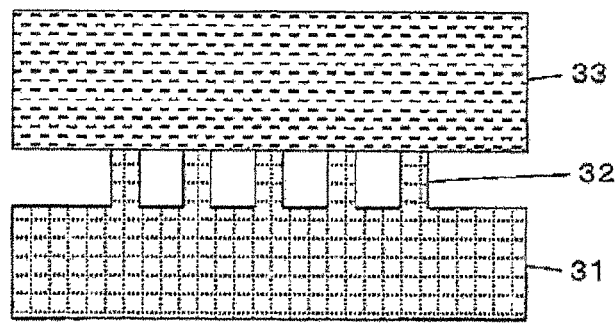
FIG. 4 is a cross section of a mold for producing an insulation sheet used in the embodiment 1.

First, a mold 31 made of Si having a protrusion structure for forming the insulation sheet 12 is produced as illustrated in FIG. 4. The protrusion structure is provided to form holes into which the electrode members 13 are filled and comprises protrusions 32 each having a cylindrical shape with a diameter of 100 μm and a height of 200 μm, and disposed and distributed in a matrix pattern having the same array pitch as the electrode 22 of the transducer 21. When only a part of the electrodes 22 of the transducer 21 are used for measuring, the mold 31 may be produced having the protrusion structure according to the positions of the electrodes 22 that are used for measuring.

The mold 31 may be produced by machining a flat Si plate using deep etching through so-called Bosch process whereby a structure of the order of micrometers can be readily produced. Alternatively, a metal mold may be produced by precision cutting or etching a metal plate.

Figure 5:
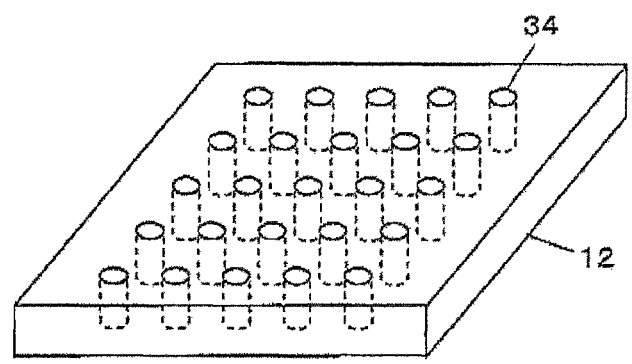
FIG. 5 is a perspective view of the insulation sheet used in the embodiment 1.
Figure 6:
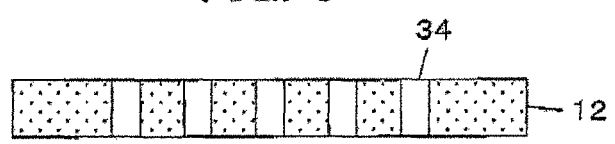
FIG. 6 is a cross section of the insulation sheet used in the embodiment 1.

To improve the demolding property of a molded product, a fluororesin-based demolding agent is applied to the surface of the mold 31 on which the protrusion structure is formed, and a flat glass plate 33 is positioned on and pressed to the protrusion structure, whereupon a thermosetting, two-component, addition polymer-type silicone rubber yet to be hardened is injected between the mold 31 and the flat plate 33. The procedure is followed by heating in an oven at 120° C. for 60 minutes to harden the silicone rubber, whereupon the molded product is released from the mold 31. FIGS. 5 and 6 illustrate the insulation sheet 12 formed in this manner. The through-holes 34 corresponding to the protrusion structure of the mold 31 are formed in a matrix pattern.

Instead of using the mold 31 and the flat plate 33, a silicone rubber sheet material may be laser-processed to form through-holes 34 and thus obtain the insulation sheet 12.

Figure 7A:
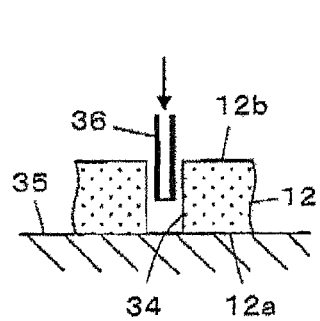
FIG. 7 is a cross section showing the steps of a method of producing electrode members.
Figure 7B:
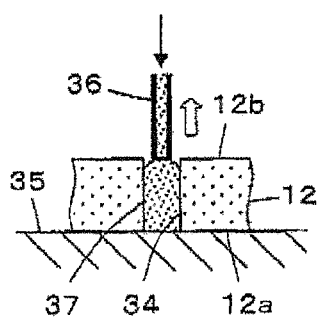
Figure 7C:
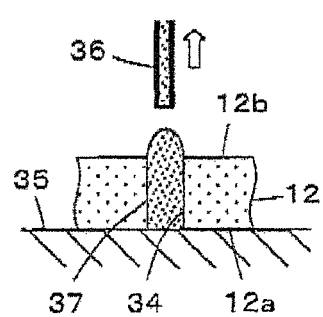

Subsequently, as illustrated in FIG. 7A, the top surface 12a of the insulation sheet 12; now turned to face downward, is adhered to the surface of a glass or Si substrate 35 having a high degree of flatness, whereupon an injection tube 36 of a dispenser is inserted into each through-hole 34 from the bottom surface side of the insulation sheet 12 to inject a silicone-based material 37 containing conductive filler such as Ag. The injection tube 36 of the dispenser has a tip whose outer diameter is smaller than the diameter 100 μm of the through-holes 34. The tip is inserted to a depth of 100 μm from the bottom surface 12b of the insulation sheet 12, i.e., halfway through the thickness of the insulation sheet 12, and thus injection is started. Then, as illustrated in FIG. 7B, injection of the silicone-based material 37 containing conductive filler is continued as the injection tube 36 is gradually lifted. Thus, the silicone-based material 37 can be allowed to project upwardly from the bottom surface 12b of the insulation sheet 12 as illustrated in FIG. 7C.

Figure 8:
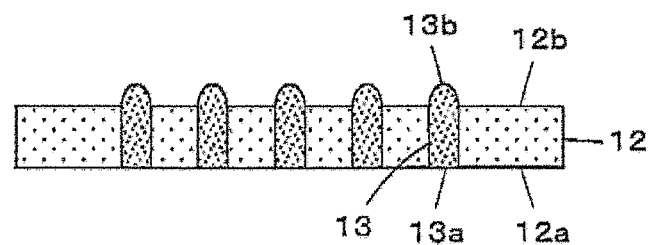
FIG. 8 is a cross section of the insulation sheet with electrode members used in the embodiment 1.

The procedure is followed by heating in an oven at 100° C. for 30 minutes to harden the silicone-based material 37. Thus, the insulation sheet 12 holding therein the electrode members 13 is produced as illustrated in FIG. 8. The one ends 13a of the electrode members 13 are in the same plane as the top surface 12a of the insulation sheet 12 while the other ends 13b project from the bottom surface 12b of the insulation sheet 12.

Because the through-holes 34 of the insulation sheet 12 made of a silicone rubber are filled with the electrode members 13 made of the silicone-based material 37 containing conductive filler, a good adhesion between the insulation sheet 12 and the electrode members 13 are ensured.

Further, a carbon paste is applied to the one ends 13a of the electrode members 13 located on the top surface side of the insulation sheet 12 while the annular liquid reservoir member 15 made of silicone rubber is adhered to the periphery of the top surface 12a of the insulation sheet 12 by a silicone rubber yet to be hardened, followed by heating and hardening in an oven at 100° C. for 60 minutes. Thus, the electrode device 11 for an electrochemical sensor chip as illustrated in FIG. 1 is produced.

Embodiment 2

Figure 9:
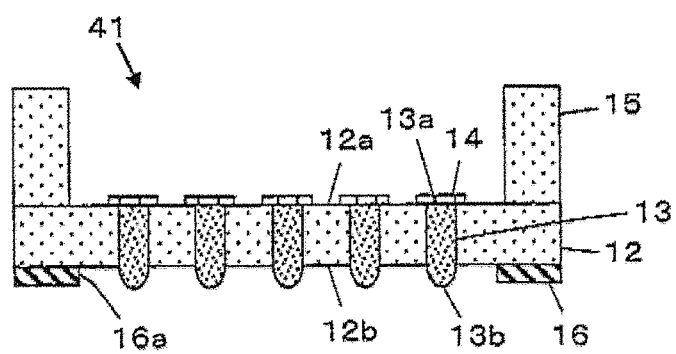
FIG. 9 is a cross section of an electrode device for an electrochemical sensor chip according to the embodiment 2.
Figure 10:
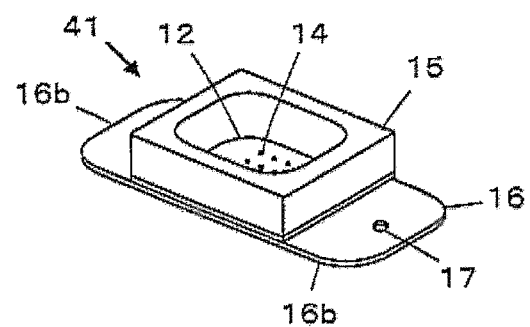
FIG. 10 is a perspective view of the electrode device for an electrochemical sensor chip according to the embodiment 2.

FIG. 9 illustrates a configuration of an electrode device 41 for an electrochemical sensor chip according to embodiment 2. The electrode device 41 for an electrochemical sensor chip is equivalent to the electrode device 11 illustrated in FIG. 1 according to the embodiment 1 except that it additionally comprises a rigid frame 16 attached to the bottom surface 12b of the insulation sheet 12 in a position close to the periphery thereof. The frame 16 has the shape of a flat sheet having an opening 16a for exposing the other ends 13b of all the electrode members 13 projecting from the bottom surface 12b of the insulation sheet 12 and comprises a pair of extensions 16b extending beyond the insulation sheet 12 and the liquid reservoir member 15 as illustrated in FIG. 10. The extensions 16b each have a positioning hole 17.

Figure 11:
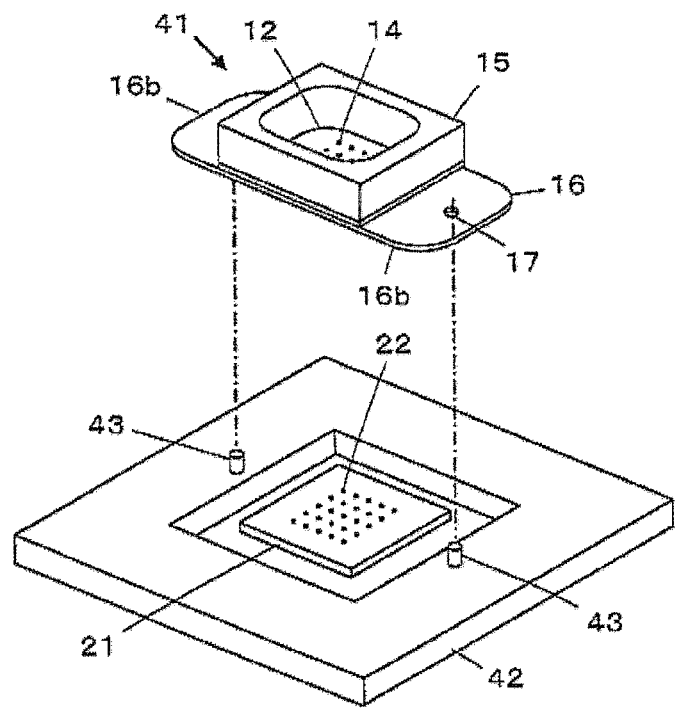
FIG. 11 is a perspective view of the electrode device for an electrochemical sensor chip according to the embodiment 2 as it is mounted to a transducer.

According to the embodiment 2, the transducer 21 is secured to a fixing base 42, and a pair of positioning pins 43 project from the fixing base 42 on the opposite sides of the transducer 21 as illustrated in FIG. 11.

Figure 12:
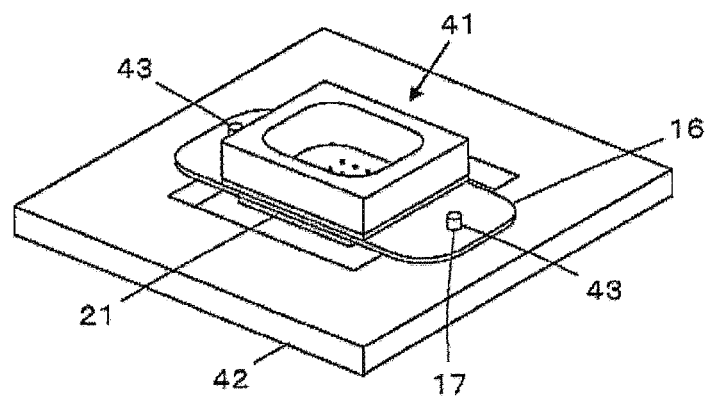
FIG. 12 is a perspective view of an electrochemical sensor chip using the electrode device for an electrochemical sensor chip according to the embodiment 2.

As illustrated in FIG. 12, the electrode device 41 for an electrochemical sensor chip and the transducer 21 can be positioned with respect to each other by inserting a pair of the positioning pins 43 of the fixing base 42 through the positioning holes 17 of the frame 16 of the electrode device 41 for an electrochemical sensor chip.

Even when the disposable electrode device 41 for an electrochemical sensor chip is replaced with a new one, the electrode device 41 for an electrochemical sensor chip and the transducer 21 can be readily positioned with respect to each other by inserting the positioning pins 43 of the fixing base 42 through the positioning holes 17 of the frame 16, provided that the electrodes 22 of the transducer 21 have been previously positioned with accuracy in relation to the positioning pins 43 of the fixing base 42 when mounting the transducer 21 on the fixing base 42, and that electrode members 13 of the electrode device 41 for an electrochemical sensor chip have been previously positioned with accuracy in relation to the positioning holes 17 of the frame 16.

The frame 16 may be made, for example, of an 80-μm thick stainless steel plate and can be attached to the bottom surface 12b of the insulation sheet 12 by insert-molding the frame 16 when forming the insulation sheet 12 using the mold 31 as described in the embodiment 1.

The diameter of the positioning holes 17 of the frame 16 and the diameter of the positioning pins 43 of the fixing base 42 may be each 1 mm, for example.

Use of the frame 16 having such a rigidity not only enables positioning of the electrode members 13 of the electrode device 41 for an electrochemical sensor chip and the electrodes 22 of the transducer 21 but facilitates handling of the electrode device 41 for an electrochemical sensor chip even when the insulation sheet 12 is made of a material having an enhanced flexibility such as silicone rubber.

Embodiment 3

Figure 13:
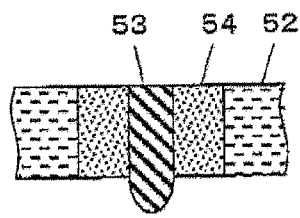
FIG. 13 is a cross section of the vicinity of one of the electrode members of an electrode device for an electrochemical sensor chip according to an embodiment 3.

While at least one of the insulation sheet 12 and the electrode members 13 preferably have elasticity, providing elastic members 54 made of a material such as silicone rubber between them as illustrated in FIG. 13 also allows an insulation sheet 52 having poor elasticity to hold electrode members 53 having poor elasticity. The elastic members 54 are so provided as to surround the respective electrode member 53. Such a structure provided with the elastic members 54 allows the electrode members 53 to displace in the insulation sheet 52 and therefore permits the use of the insulation sheet 52 made of a hard material such as acrylic, polycarbonate, glass, or ceramics and the use of the electrode members 53 made of a metallic material coated by Au to establish a good electric connection between the electrode members 53 held by the insulation sheet 52 and the electrodes 22 of the transducer 21.

Figure 14:
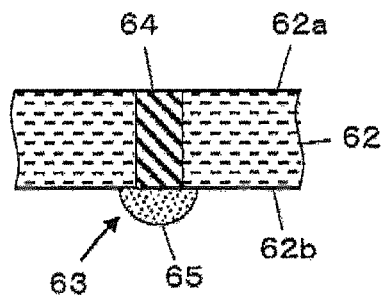
FIG. 14 is a cross section of the vicinity of one of the electrode members of an electrode device for an electrochemical sensor chip according to a modification of the embodiment 3.
Figure 15:
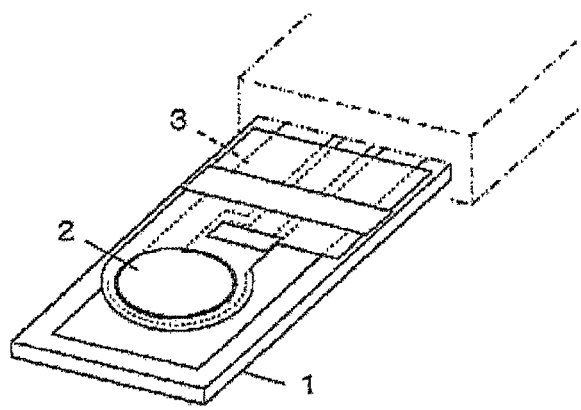
FIG. 15 is a perspective view of a conventional electrode device for an electrochemical sensor chip.
Figure 16:
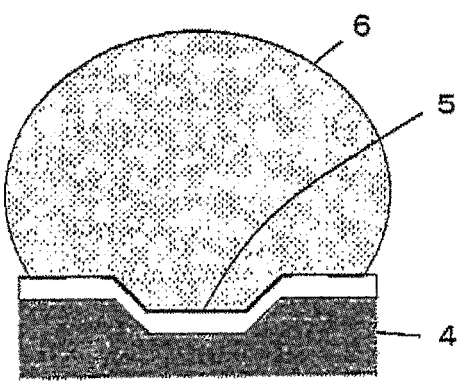
FIG. 16 is a cross section of a part of another conventional electrode device for an electrochemical sensor chip.

Alternatively, another configuration may be made such that, as illustrated in FIG. 14, an insulation sheet 62 having poor elasticity directly holds metallic members 64 having poor elasticity without providing elastic members therebetween, both ends of each metallic member 64 are positioned in the same planes as a top surface 62a and a bottom surface 62b of the insulation sheet 62 so that neither end of each metallic member 64 protrudes from the insulation sheet 62, and a conductive member 65 having elasticity is formed on one ends of each metallic member 64 located on the bottom surface side 62b of the insulation sheet 62 so as to project from the insulation sheet 62. The metallic members 64 and the conductive members 65 constitute electrode members 63.

The conductors 64 having elasticity may be formed of a silicone based material containing conductive filler such as Ag. The insulation sheet 62 may be made of hard materials such as acrylic, polycarbonate, glass, and ceramics; the metallic members 64 may be made of a metallic material coated by Au.

Such a structure also enables a good electric connection to be established between the electrode members 63 held by the insulation sheet 62 and the electrodes 22 of the transducer 21.

What is claimed is:

1. An electrode device for an electrochemical sensor chip for electrically connecting an analyte to electrodes formed on a surface of a transducer, comprising:

an insulation sheet having an insulating property and including a top surface and a bottom surface opposite to each other in a thickness direction; and electrode members having a conductivity and held by the insulation sheet with the electrode members piercing the insulation sheet in the thickness direction, one ends of the electrode members located on the top surface side of the insulation sheet being connected to the analyte, the other ends located on the bottom surface side of the insulation sheet being connected to the electrodes of the transducer, wherein the other ends of the electrode members each have a projecting portion protruding from the bottom surface of the insulation sheet, and the whole of each of the electrode members is elastic.

2. The electrode device for an electrochemical sensor chip according to claim 1, wherein the electrode members are in intimate contact with the insulation sheet so that a liquid sample containing the analyte does not leak to the bottom surface side of the insulation sheet.

3. The electrode device for an electrochemical sensor chip according to claim 1, wherein the one ends of the electrode members are covered by a conductive biocompatible coating.

4. The electrode device for an electrochemical sensor chip according to claim 1, further comprising a liquid reservoir member provided on a periphery of the top surface of the insulation sheet.

5. An electrode device for an electrochemical sensor chip for electrically connecting an analyte to electrodes formed on a surface of a transducer, comprising:

an insulation sheet having an insulating property and including a top surface and a bottom surface opposite to each other in a thickness direction; and electrode members having a conductivity and held by the insulation sheet with the electrode members piercing the insulation sheet in the thickness direction, one ends of the electrode members located on the top surface side of the insulation sheet being connected to the analyte, the other ends located on the bottom surface side of the insulation sheet being connected to the electrodes of the transducer, wherein the insulation sheet is elastic.

6. The electrode device for an electrochemical sensor chip according to claim 5, wherein the bottom surface of the insulation sheet has an adhesion.

7. The electrode device for an electrochemical sensor chip according to claim 5, wherein the other ends of the electrode members each have a projecting portion protruding from the bottom surface of the insulation sheet.

8. The electrode device for an electrochemical sensor chip according to claim 5, wherein the electrode members are in intimate contact with the insulation sheet so that a liquid sample containing the analyte does not leak to the bottom surface side of the insulation sheet.

9. The electrode device for an electrochemical sensor chip according to claim 5, wherein the one ends of the electrode members are covered by a conductive biocompatible coating.

10. The electrode device for an electrochemical sensor chip according to claim 5, further comprising a liquid reservoir member provided on a periphery of the top surface of the insulation sheet.

11. The electrode device for an electrochemical sensor chip according to claim 5, further comprising a rigid frame attached to a periphery of the bottom surface of the insulation sheet.

12. An electrode device for an electrochemical sensor chip for electrically connecting an analyte to electrodes formed on a surface of a transducer, comprising:
- an insulation sheet having an insulating property and including a top surface and a bottom surface opposite to each other in a thickness direction;
- electrode members having a conductivity and held by the insulation sheet with the electrode members piercing the insulation sheet in the thickness direction, one ends of the electrode members located on the top surface side of the insulation sheet being connected to the analyte, the other ends located on the bottom surface side of the insulation sheet being connected to the electrodes of the transducer; and
- a rigid frame attached to a periphery of the bottom surface of the insulation sheet.

13. The electrode device for an electrochemical sensor chip according to claim 12, wherein the other ends of the electrode members each have a projecting portion protruding from the bottom surface of the insulation sheet.

14. An electrode device for an electrochemical sensor chip for electrically connecting an analyte to electrodes formed on a surface of a transducer, comprising:
- an insulation sheet having an insulating property and including a top surface and a bottom surface opposite to each other in a thickness direction;
- electrode members having a conductivity and held by the insulation sheet with the electrode members piercing the insulation sheet in the thickness direction, one ends of the electrode members located on the top surface side of the insulation sheet being connected to the analyte, the other ends located on the bottom surface side of the insulation sheet being connected to the electrodes of the transducer; and
- elastic members provided between the insulation sheet and the electrode members so as to surround each one of the electrode members.

15. The electrode device for an electrochemical sensor chip according to claim 14, wherein the other ends of the electrode members each have a projecting portion protruding from the bottom surface of the insulation sheet.

16. The electrode device for an electrochemical sensor chip according to claim 14, wherein the electrode members are in intimate contact with the insulation sheet so that a liquid sample containing the analyte does not leak to the bottom surface side of the insulation sheet.

17. The electrode device for an electrochemical sensor chip according to claim 14, wherein the one ends of the electrode members are covered by a conductive biocompatible coating.

18. The electrode device for an electrochemical sensor chip according to claim 14, further comprising a liquid reservoir member provided on a periphery of the top surface of the insulation sheet.

19. The electrode device for an electrochemical sensor chip according to claim 14, further comprising a rigid frame attached to a periphery of the bottom surface of the insulation sheet.

* * * * *